(12) United States Patent
Koester et al.

(10) Patent No.: US 8,038,895 B2
(45) Date of Patent: Oct. 18, 2011

(54) METHOD AND APPARTUS FOR DETECTION OF MECHANICAL DEFECTS IN AN INGOT PIECE COMPOSED OF SEMICONDUCTOR MATERIAL

(75) Inventors: Ludwig Koester, Burghausen (DE); Peter Czurratis, Aalen (DE); Klaus Kraemer, Herborn (DE)

(73) Assignee: Siltronic AG, Munich (DE)

( * ) Notice: Subject to any disclaimer, the term of this patent is extended or adjusted under 35 U.S.C. 154(b) by 1096 days.

(21) Appl. No.: 11/764,854

(22) Filed: Jun. 19, 2007

(65) Prior Publication Data
US 2008/0041159 A1     Feb. 21, 2008

(30) Foreign Application Priority Data

Jun. 22, 2006 (DE) .......................... 10 2006 028 650
Jul. 13, 2006 (DE) .......................... 10 2006 032 431

(51) Int. Cl.
*B31D 3/00* (2006.01)
(52) U.S. Cl. ................ 216/56; 216/60; 216/84; 216/85; 117/14; 117/38
(58) Field of Classification Search .................... 216/59, 216/60, 84, 85; 117/14, 38
See application file for complete search history.

(56) References Cited

U.S. PATENT DOCUMENTS

| | | | |
|---|---|---|---|
| 4,028,933 A | 6/1977 | Lemons et al. | |
| 4,370,889 A | 2/1983 | Ruthrof et al. | |
| 5,381,693 A | 1/1995 | Kobayashi et al. | |
| 6,047,600 A | 4/2000 | Ottosson et al. | |
| 6,112,738 A * | 9/2000 | Witte et al. ................ | 125/16.02 |
| 6,439,054 B1 | 8/2002 | Gore et al. | |
| 2004/0021097 A1* | 2/2004 | Preece ........................ | 250/559.4 |
| 2005/0252441 A1* | 11/2005 | Sakurada et al. ................ | 117/13 |
| 2006/0123912 A1* | 6/2006 | Karasawa et al. ................ | 73/602 |
| 2007/0243695 A1 | 10/2007 | Iida | |
| 2008/0302295 A1* | 12/2008 | Kotooka et al. .................. | 117/14 |

FOREIGN PATENT DOCUMENTS

| | | |
|---|---|---|
| DE | 25 04 988 | 1/1976 |
| DE | 29 36 882 A1 | 4/1981 |
| DE | 10 2006 005 448 A1 | 10/2006 |
| EP | 0102176 A1 | 3/1984 |
| JP | 49019940 B | 5/1974 |
| JP | 5917154 A | 1/1984 |

(Continued)

OTHER PUBLICATIONS

English Derwent Abstract AN 2006-783817 corresponding to DE 10 2006 005 448 A1.

*Primary Examiner* — Binh X Tran
(74) *Attorney, Agent, or Firm* — Brooks Kushman P.C.

(57) ABSTRACT

A method for detection of mechanical defects in a semiconductor ingot section which has at least one planar surface, and a thickness at right angles to this surface of 1 cm to 100 cm, involves scanning the planar surface by at least one ultrasound head which is coupled via a liquid coupling medium to the planar surface and, at each measurement point (x,y) producing at least one ultrasound pulse which is directed at the planar surface of the ingot section, recording the ultrasound-pulse echo as a function of time, such that an echo from the planar surface, an echo from a surface opposite the planar surface, and further echoes are detected, with the positions $(x_p, y_p, z_p)$ of mechanical defects in the ingot section being determined from the further echoes.

11 Claims, 3 Drawing Sheets

FOREIGN PATENT DOCUMENTS

| | | |
|---|---|---|
| JP | 59060354 A | 4/1984 |
| JP | 61241659 A | 10/1986 |
| JP | 63121748 A | 5/1988 |
| JP | 02238356 A | 9/1990 |
| JP | 2002340865 | 11/2002 |
| JP | 2004279144 | 7/2004 |
| JP | 2004233279 | 8/2004 |
| KR | 199984235 | 12/1999 |
| WO | WO 01/86281 A1 | 11/2001 |
| WO | WO 02/40987 A1 | 5/2002 |
| WO | 2005076333 A1 | 8/2005 |
| WO | WO 2006013828 A1 * | 2/2006 |

* cited by examiner

METHOD AND APPARTUS FOR DETECTION OF MECHANICAL DEFECTS IN AN INGOT PIECE COMPOSED OF SEMICONDUCTOR MATERIAL

BACKGROUND OF THE INVENTION

1. Field of the Invention

The invention relates to a method and an apparatus for detection of mechanical defects in an ingot section composed of semiconductor material.

2. Background Art

In microelectronics, wafers which are composed of a semiconductor material are used as substrates for the production of microelectronic components. Suitable materials are, for example, II/VI compound semiconductors, III/V compound semiconductors or element semiconductors such as germanium or the particularly useful silicon.

The semiconductor wafers are produced by first of all cutting a single-crystal semiconductor ingot into ingot sections with a length of several centimeters up to several tens of centimeters. These ingot sections are then cut into thin wafers with a thickness of about 1 millimeter. Single-crystal semiconductor ingots are produced either without the use of a crucible by means of the so-called float-zone (FZ) process, or by means of the Czochralski crucible-pulling method. Particularly in the case of the Czochralski crucible-pulling method, it is possible for gas bubbles to become trapped in the growing semiconductor ingot. These gas bubbles represent gas-filled cavities in the form of bubbles in the semiconductor ingot, and may have diameters from about 10 µm up to about 10 mm. These gas bubbles are in some cases cut into when the semiconductor ingot is being cut into wafers, so that they are visible on the surface of the semiconductor wafers. Defective semiconductor wafers such as these are segregated before delivery, and are not used for the production of microelectronic components.

Others of the gas bubbles are, however, not cut into during the cutting process, so that the gas bubbles remain as small cavities in the affected semiconductor wafers, although no defect is externally visible. If semiconductor wafers such as these are used for production of microelectronic components, then, depending on their position in the semiconductor wafer, the cavities can lead to failure of individual components, thus reducing the yield from component manufacture.

In order to avoid this, a test method has been used according to the prior art for semiconductor wafers composed of silicon, by means of which each individual completely processed semiconductor wafer is checked for the presence of cavities, before it is delivered and is used for production of components. This method is based on the illumination of one end of the semiconductor wafer with infrared radiation, and the measurement and imaging of the transmission, that is to say of the intensity of the transmitted radiation, on the other end of the semiconductor wafer. Infrared radiation is transmitted through the semiconductor material, with the light being refracted on the boundary surface of a cavity, leading to reduced transmission. This method can be used only for semiconductor materials through which infrared radiation can pass.

This method is applied to surfaces with little roughness, in order to avoid severe light scattering on the surface, and thus reduced transmission. This means that the semiconductor wafers cannot be examined directly after their production by cutting of the ingot sections, but only after further processing steps which smooth the surface, and in the extreme only after they have been polished at the end of the production process. Semiconductor wafers with cavities therefore have to pass through an unnecessarily large number of processing steps before they can be segregated and rejected. However, earlier segregation would be desirable, in order to avoid the costs associated with the processing of defective semiconductor wafers.

The previously described test method also is relatively costly, since it must be carried out on each individual semiconductor wafer. Furthermore, the described method is subject to further restrictions relating to the dopant content, since the light is absorbed by the charge carriers which are released as the dopant content increases, thus greatly reducing the transmitted light intensity.

An ultrasound test method is also known in the prior art, by means of which various mechanical defects are detected in different materials. Until now, the imaging of defects has been restricted to worksection thicknesses of a few millimeters, because the sensitivity of the method decreases at greater depths.

Scanning ultrasound microscopes in which a sample is scanned two-dimensionally by means of ultrasound and in which the sound waves that pass through or are reflected are processed in order to produce an image from them are known from the prior art, for example from DE2504988A1, and international patent application WO01/86281A1 discloses a scanning ultrasound microscope which produces three-dimensional images of a sample. In this case, the images are produced non-destructively, thus resulting in information about the internal structure of a sample. However, the prior art described above is not designed for high-speed data recording of the samples to be examined and for measurement of ingot sections with a length of up to 100 cm. Furthermore, the apparatuses according to the prior art have a limited throughput.

SUMMARY OF THE INVENTION

An object of the invention is therefore to provide a method which can be applied to all types of semiconductor materials, and which allows early segregation of those semiconductor wafers which have cavities. The invention is therefore based on the object of providing an apparatus for acoustic scanning microscopy, which reduces the measurement time per sample and at the same time allows reliable detection.

DETAILED DESCRIPTION OF THE PREFERRED EMBODIMENT(S)

Figure 1:
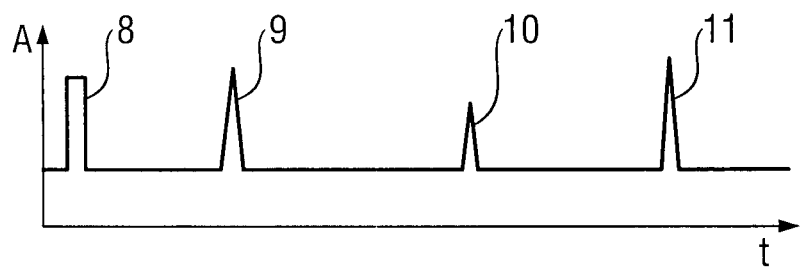
FIG. 1 shows, schematically, the measurement signal obtained when carrying out the method according to the invention.

Thus, one aspect of the invention comprises, referring to the drawing Figures, a method for detection of mechanical defects 4 in an ingot section 1 which is composed of semiconductor material and has at least one planar surface 6 and a thickness, measured at right angles to this surface, of 1 cm to 100 cm, with the planar surface 6 of the ingot section 1 being scanned during the method by at least one ultrasound head 2 which is coupled via a liquid coupling medium 3 to the planar surface 6 of the ingot section 1 and, at each measurement point x,y produces at least one ultrasound pulse 8 which is directed at the planar surface 6 of the ingot section 1, the ultrasound-pulse echo originating from the ingot section 1 being recorded as a function of time, such that an echo 9 from the planar surface 6, an echo 11 from a surface 7, opposite the planar surface, of the ingot section 6 and, possibly, further echoes 10 are detected, with the positions $x_p$, $y_p$, $z_p$ of mechanical defects 4 in the ingot section 1 being determined from the further echoes 10.

For the purposes of the present invention, the expression "an ingot section" means a worksection composed of semiconductor material which has larger dimensions at least in one direction than a typical semiconductor wafer. Ingot sections are typically produced by cutting a semiconductor ingot at right angles to its longitudinal axis, that is to say at right angles to its outer surface. If the ingot sections are composed of single-crystal semiconductor material, then they are generally in the form of an essentially straight circular cylinder. If the semiconductor material is single-crystal silicon, the diameter of the ingot sections is generally between 100 and 450 mm. The length of the ingot sections is 1 cm to 100 cm, with lengths of up to 50 cm being preferred for the examination method according to the invention. However, particularly in the case of multicrystalline or polycrystalline semiconductor material, the ingot sections may also be in the form of an elongated cuboid, which has rectangular or square end surfaces.

Single-crystal ingot sections 1 (see FIG. 2) generally have two planar end surfaces 6, 7 and a curved outer surface 5. At least one planar surface 6 is required in order to carry out the method according to the invention. In the method according to the invention, this planar surface 6 is scanned by at least one ultrasound head 2 (also referred to as a transducer). The ultrasound head 2 makes contact with the planar surface 6 via a liquid coupling medium 3, preferably water. The ultrasound head 2 produces at least one ultrasound pulse 8 (FIG. 1), which is directed at the planar surface 6 of the ingot section generally by means of a piezoelectric transducer layer, at each measurement point x,y. The echoes 9, 10, 11 which return from the ingot section are in turn detected by the ultrasound head 2. Further echoes 10, which result from mechanical defects 4 in the ingot section, may be detected in addition to the echoes 9, 11 which are produced by the planar surface 6 and an opposite surface of the ingot section (for example the opposite second end surface 7 in the case of cylindrical ingot sections). The distance $z_p$ between the defect 4 and the planar surface 6 in the z direction can be calculated from the delay time t of the echoes 10. FIG. 1 shows the amplitude A of the signal plotted as a function of the delay time t. The position $x_p, y_p$ of the defect 4 on the x,y plane (essentially parallel to the planar surface 6) is determined from the instantaneous position of the ultrasound head 2. The spatial position of the defect 4 can thus be determined unambiguously. In order to obtain information about the entire ingot section 1, the planar surface 6 is scanned by means of the ultrasound head 2. During the scanning process, the at least one ultrasound head 2 is preferably moved on a plane (referred to in the following text as the scanning plane 17, see FIG. 5) which is at right angles to the outer surface 5 of the ingot section. This measurement principle is referred to as scanning ultrasound microscopy or scanning acoustic microscopy, and is known from the prior art cited above.

Mechanical defects which can be detected and located by means of scanning ultrasound microscopy are all areas within an ingot section whose sound propagation characteristics differ from the undisturbed semiconductor material. These include, for example, cracks and, in particular, the cavities described above. The method can be used to detect cavities with a diameter of $\geqq 100$ μm, and even $\geqq 50$ μm.

Figure 3:
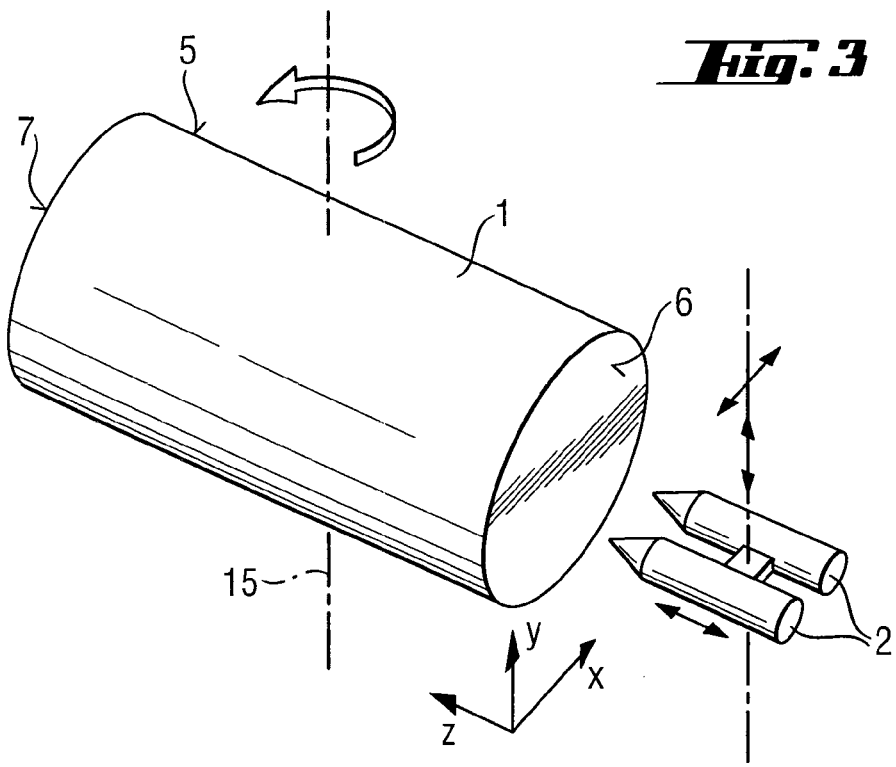
FIG. 3 shows, schematically, a first embodiment of the scanning ultrasound microscope according to the invention, with two ultrasound heads.

In order to allow material thicknesses which are as large as possible to be examined, for example up to 50 cm, the ultrasound is preferably not focused, or is only slightly focused. The ultrasound pulses should therefore preferably be focused on a surface 7 which is a long distance from the planar surface 6, in the ideal case on a surface 7 which is located opposite the planar surface 6, that is to say on the rear end surface of the ingot section 1. In this case, slightly focusing or non-focusing ultrasound heads 2 can be used in conjunction with modified A/D converters. If the ingot section 1 is examined from only one end, the time period for the recording of the echo should be chosen such that the echo 11 (FIG. 1) still includes the opposite surface 7 of the ingot section 1 (FIG. 3).

Figure 4:
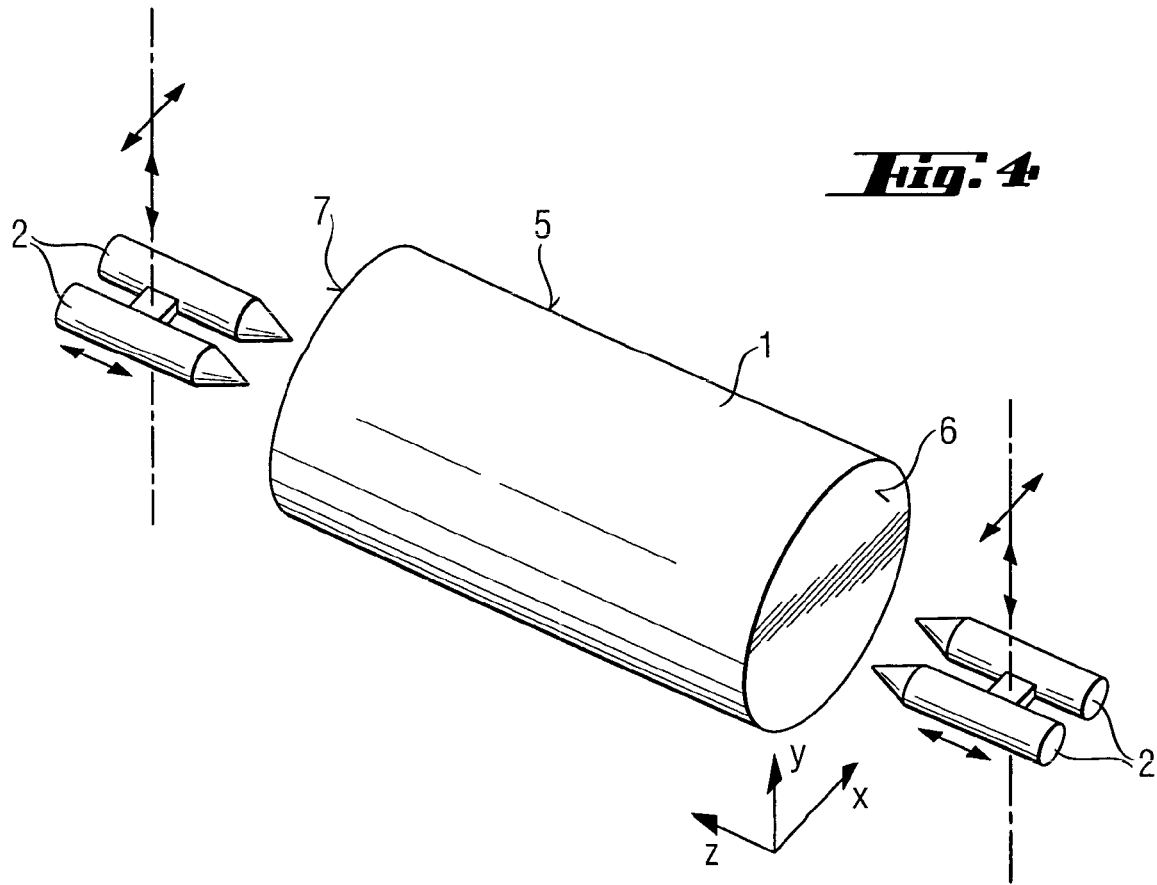
FIG. 4 shows, schematically, a second embodiment of the scanning ultrasound microscope according to the invention, with two ultrasound heads on in each case two opposite planar surfaces of the sample.

In order to increase the verification sensitivity, the ingot section can be examined from both ends, preferably for lengths of more than 20 cm. If the length of the ingot section is more than 50 cm, a measurement is required on both planar end surfaces 6, 7, in order to obtain information about the entire volume of the ingot section. In order to measure an ingot section 1 from both ends, it is first of all scanned from the first planar surface 6 by means of the at least one ultrasound head 2, after which the ingot section 1 is rotated by means of a rotation apparatus through 180° about an axis 15 which is at right angles to the longitudinal axis of the ingot section, after which the second planar surface 7 is scanned (FIG. 3). Another option is to use two opposite ultrasound heads 2 for scanning, or to use two opposite arrangements of a plurality of ultrasound heads 2. In this case, the ingot section is not rotated (FIG. 4).

If the semiconductor material is single-crystal silicon, then the propagation speed of the ultrasound is approximately 8500 m/s. The required duration for recording of the sound echo is determined from the length of the ingot section to be examined. By way of example, if an ingot section with a length of 20 cm is measured from one end or an ingot section with a length of 40 cm is measured from both ends, this requires a recording duration of about 100 μs with a time resolution of at least 10 ns, preferably at least 1 ns, in order to obtain information about the entire length of the ingot section and in order to determine the position $z_p$ of the cavity in the z direction of the ingot section from the echo delay time. A suitable evaluation window is preferably defined in order to exclude those signals 9, 11 (see FIG. 1) which are produced by the surfaces of the ingot section for the evaluation of the detected sound echo. The evaluated sound echo and thus the examined volume of the ingot section is subdivided into n segments in the z direction by means of evaluation windows of limited time, in which segment the sound signal can be integrated in order to improve the signal-to-noise ratio. The chosen window length multiplied by n therefore represents the entire ensonified volume of the ingot section.

Figure 5:
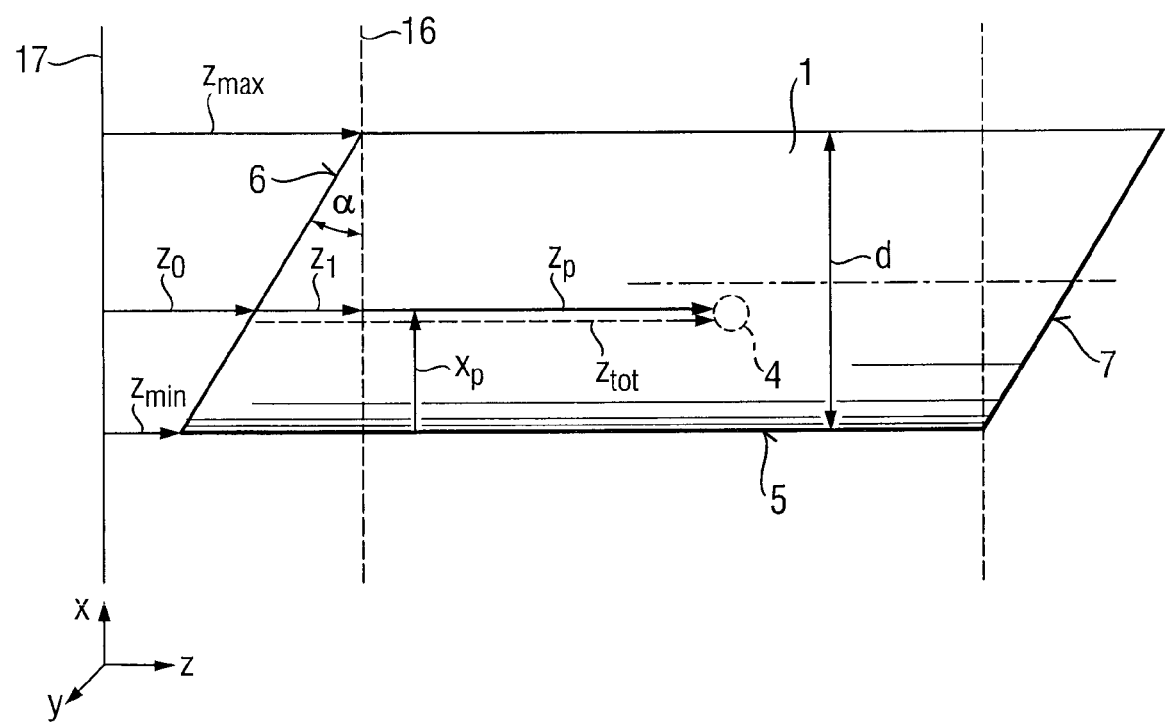
FIG. 5 shows, schematically, the wedge angle of an ingot section and the parameters for determination of the wedge angle and of the position of the reference plane.

If it is not certain the planar surface 6 is at right angles to the outer surface 5 of the ingot section, it is preferable to evaluate the surface signals 9, 11 (FIG. 1) as illustrated in FIG. 5 in order to determine the wedge angle of the ingot section, which is caused by the uncertainty in the crystal axis and the sawing process. Because of this wedge angle, it is not simply possible to use one of the end faces 6, 7 as the reference plane 16 for the determination process as described further below of which of the semiconductor wafers that will be produced later from the ingot section will be affected by mechanical defects. That plane which is located at right angles to the outer surface 5 and is closest to the end surface 6 but just no longer intersects it is therefore defined as the reference plane 16. If the scanning plane 17 of the ultrasound head is chosen to be at right angles to the outer surface 5 of the ingot section 1, the wedge angle α over the diameter d of the ingot section 1 can easily be determined using the relationship $\tan(\alpha)=(z_{max}-z_{min})/d$ from the delay time difference between the longest and shortest delay time of the echo from that planar surface 6 of the ingot section 1 which faces the ultrasound head. The maximum distance $z_{max}$ between the scanning plane 17 and the planar surface 6 is determined from the longest delay time, and the shortest distance $z_{min}$ is determined from the shortest delay time.

In order to ensure that the scanning plane is at right angles to the outer surface of the ingot section, the ingot section is aligned before the start of the measurement. This can be done, for example, by means of an appropriately adjusted depression in the form of a trough, into which the outer surface of the ingot section is placed, and which aligns the ingot section exactly.

The distance $z_p$ between a mechanical defect 4 detected at the position $x_p,y_p$ and the reference plane 16 can be determined easily, if the wedge angle is known, from the relationships:

$$z_1=\tan(\alpha)\cdot(d-x_p)$$

$$z_0=z_{max}-z_1$$

$$z_p=z_{tot}-z_1$$

In this case, $z_1$ represents the distance between the planar surface 6 and the reference plane 16, $z_0$ the distance between the ultrasound head, which is located at the point x,y on the scanning plane 17, and the planar surface 6, and $z_{tot}$ the distance between the detected defect 4 and the planar surface 6. All of the distances mentioned are measured parallel to the outer surface.

Contrary to previous experience, on the basis of which scanning ultrasound microscopy is suitable only for the examination of relatively thin layers close to the surface, it has been found that the method can also be used, particularly in the case of single-crystal semiconductor material, for examination of material thicknesses of up to 25 cm, or even of up to 50 cm. This is explained by the high quality and freedom from defects of the semiconductor monocrystal, which leads to undisturbed ballistic sound propagation over long distances and in preferred directions. Individual mechanical defects can therefore be located very well, even at great depths. In this case, there are no further restrictions relating to the characteristics of the ingot sections, for example the diameter, the crystal orientation or the doping.

An apparatus which also achieves an embodiment on which the invention is based can be used to carry out the method according to the invention. In one embodiment, the apparatus comprises a scanning ultrasound microscope having a holding apparatus for an ingot section 1 which is to be examined and has at least one planar surface 6 lying on the x,y plane, having at least two ultrasound heads 2 for production and detection of an ultrasound signal, having a first mounting apparatus on which the at least two ultrasound heads are mounted such that they cannot move in the x,y direction, having an adjustment device, by means of which the ultrasound heads 2 can be moved in the z direction at right angles to the x,y plane relative to the holding apparatus, having a movement device, by means of which the mounting apparatus and the holding apparatus can be moved relative to one another in the x,y direction, having a control unit 12 for control of the movement device and of the adjustment device, as well as an evaluation unit for processing of the ultrasound signal detected by the ultrasound heads 2.

The use of an apparatus such as this is advantageous because a plurality of different x,y positions on an ingot section are examined at the same time, with the various positions being ensonified with acoustic signals from one ultrasound head in each case, and with their echoes each being detected by the respective ultrasound head. This makes it possible to achieve a significant reduction in the measurement time.

Figure 2:
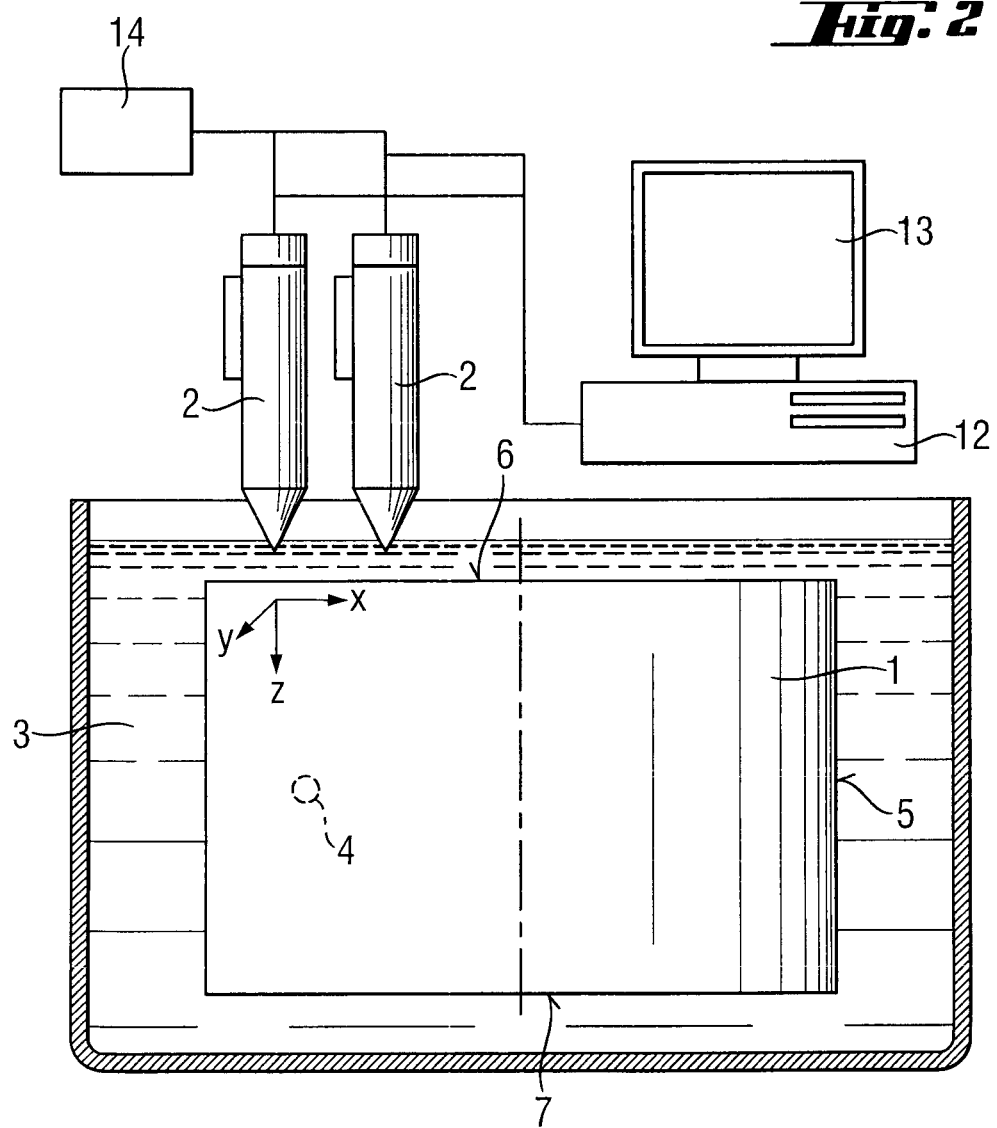
FIG. 2 shows, schematically, a scanning ultrasound microscope according to the invention.

One embodiment of a scanning ultrasound microscope according to the invention will be described in the following text with reference to FIG. 2. The scanning ultrasound microscope has a holding apparatus for an ingot section 1 which is to be examined and has at least one planar surface 6 which essentially lies on the x,y plane. It therefore differs from the prior art by having at least two ultrasound heads 2 for production and detection of an ultrasound signal. It is also possible to use more, for example four, ultrasound heads. One of the ultrasound heads is preferably a so-called master transducer, and all of the others are slave transducers. The ultrasound heads are preferably supplied with a high-frequency AC voltage from a high-frequency generator 14, and this is converted by a piezoelectric transducer layer to an acoustic signal in the form of an ultrasound pulse. The echoes which are reflected from an element of the ingot section 1 at a different depth are then in turn detected by the piezoelectric transducer layer of the respective ultrasound head 2, and are converted to an electrical signal. This signal is preferably digitized by means of an A/D converter and is transmitted to the evaluation unit, which records it as a function of the instantaneous examined position on the x,y plane. The ultrasound frequency is preferably in the range from 5 to 25 MHz. Multiple 100 MHz re-interfaces can also be used for ultrasound heads up to 25 MHZ. The at least two ultrasound heads 2 are mounted on a first mounting apparatus, such that they cannot move in the x,y direction.

It is possible to provide a joint adjustment device for all of the ultrasound heads 2. In this case, all that is possible is to adjust all of the ultrasound heads jointly in the z direction. However, a dedicated adjustment device is preferably provided for each of the ultrasound heads 2, by means of which the ultrasound head 2 can be moved in the z direction at right angles to the x,y plane, independently of the other ultrasound heads 2, relative to the mounting apparatus. Each ultrasound head can then be adjusted independently in the z direction, in such a manner that it detects a maximum signal intensity (for example a maximum signal intensity of the echo from the rear planar surface 7). Each adjustment device preferably has an independent motor drive. The apparatus also contains an x,y scanning apparatus, which can at the same time keep the two or more ultrasound heads in focus, in order to provide open-loop and closed-loop control for them at the focus position, independently of one another, for example as disclosed in German patent application 1020060054482.

In order to allow scanning of the planar surface 6 of the ingot section, the scanning ultrasound microscope according to the invention has a movement device, by means of which the mounting apparatus and the holding apparatus for the ingot section can be moved relative to one another in the x,y directions. The planar surface 6 of the ingot section is in this case scanned measurement point by measurement point, and line by line, so that the entire planar surface of the ingot section is covered.

Furthermore, a control unit is provided for control of the movement device and of the adjustment device, as well as an evaluation unit for processing of the ultrasound signal detected by the ultrasound heads. The control unit and the evaluation unit may be combined in one unit, for example in a computer 12 with monitor 13. The echoes detected by the two or more ultrasound heads are preferably processed and recorded simultaneously, with the detected signals being recorded as a function of the instantaneously examined position on the x,y plane, and with the position $x_p$, $y_p$, $z_p$ of the mechanical defects being determined from this. The data items for an image display are preferably produced simultaneously.

A modified scanning ultrasound microscope is preferably used for examination of ingot sections 1 with a length of more than 20 cm, having a further mounting apparatus on which at least two further ultrasound heads 2 are mounted, analogously to the first mounting apparatus. The second mounting apparatus is arranged such that the ultrasound heads 2 mounted on it can examine a second planar surface 7 of the ingot section 1, as illustrated in FIG. 4.

Depending on the nature of the semiconductor material, the apparatus according to the invention can be used to examine ingot sections with a diameter of up to 450 mm, and with a length of up to 40 cm or more (if the examination is carried out from both ends), or up to 20 cm (if the examination is carried out from one end), or even with a length of up to 50 cm or 25 cm, respectively, or 100 cm or 50 cm, respectively.

The method according to the invention and the apparatus according to the invention make it possible to segregate semiconductor wafers affected by mechanical defects, for example cavities, at an early stage in the production process without having to individually examine all of the semiconductor wafers, and having to subject those semiconductor wafers which are affected by the defects to further and unnecessary processing steps. This results in considerable time and cost advantages.

The invention therefore also relates to a method for production of a multiplicity of semiconductor wafers, comprising the following steps in the stated sequence:

a) producing a semiconductor ingot, b) cutting the semiconductor ingot into ingot sections with a length of 1 cm to 100 cm, d) determining the position of mechanical defects in each ingot section, with the position of each defect being defined uniquely by coordinates $x_p$, $y_p$ on a plane parallel to the cuts to be made in step f), as well as by a coordinate $z_p$ at right angles to this plane, f) cutting the ingot sections into a multiplicity of semiconductor wafers with a thickness of 0.2 to 2 mm, and h) segregating those semiconductor wafers which contain the positions at which mechanical defects have been found.

The individual steps of this method according to the invention for production of a multiplicity of semiconductor wafers will be described in detail in the following text:

First of all, a semiconductor ingot is produced in step a). The semiconductor ingot is preferably single-crystal. The semiconductor ingot is preferably composed of silicon, in particular single-crystal silicon. In this case, the semiconductor ingot generally has a diameter from about 100 to 450 mm, and is produced, for example, by means of the float zone process or by means of the Czochralski crucible-pulling process. Since the described cavities occur predominantly when using Czochralski-pulled single-crystal semiconductor ingots, it is preferable for the inventive method to be applied to semiconductor ingots such as these. However, the method is also applicable to cast, multicrystalline or polycrystalline semiconductor ingots (which are also referred to as blocks), which are used for example in the production of solar cells.

The semiconductor ingot is cut into ingot sections in step b), which have a length from 1 cm to 100 cm, preferably to 50 cm. The cuts are generally made using a bandsaw or internal-diameter saw, and the ingot is generally cut into sections at right angles to its longitudinal axis. In the case of a semiconductor ingot having a round cross section, this means that the ingot sections are essentially in the form of a straight ("right") circular cylinder. As a result of the pulling process, the ingot sections have certain irregularities, however.

In general, an optional step c) is carried out after step b), in which the outer surfaces of the essentially cylindrical ingot sections are ground such that the ingot sections have an exactly cylindrical shape. In addition, orientation features such as orientation notches or orientation flats can be produced on the outer surface of the ingot sections. This step can be carried out after, but preferably before, step d).

The position of mechanical defects in each ingot section is determined in step d). This is preferably done using scanning ultrasound microscopy as described above.

Alternatively, the position of mechanical defects, in particular of cavities, can be determined by illuminating one end of the ingot section with infrared radiation and by measuring the transmission at the other end of the ingot section. This measurement is preferably carried out on the outer surface of the cylindrical ingot section, in order to avoid the light from having to pass over excessively long distances. Since excessive roughness interferes with this measurement, it is preferable to smooth the relevant surfaces of the ingot section before the measurement by fine-grinding, etching, polishing or a suitable combination of these processes. The roughness of the relevant surfaces should preferably not exceed Ra=0.2 µm. In this method, images of the interior of the ingot section are produced using an infrared-sensitive camera with a suitable objective. Gas enclosures or defects in the interior lead to refraction or absorption of the incident light. The depth of the defects is determined by the objective setting which results in a focused image.

Since additional smoothing of the surface is required for use of the infrared transmission method, the use of scanning ultrasound microscopy is preferable in step d).

In step f), the ingot section, possibly together with further ingot sections, is cut into semiconductor wafers, in a corresponding manner to the prior art, with a thickness of 0.2 to 2 mm. This is preferably done by means of a multi wire saw (MWS) according to the prior art. The ingot sections are preferably cut into semiconductor wafers at right angles to their outer surfaces. The semiconductor wafers are then generally cleaned and separated, that is to say the semiconductor wafers which are in the form of packs after the multi wire saw process are separated, and are individually placed in the compartments of a cassette or of a magazine.

In step h), those semiconductor wafers which contain the positions at which cavities were found in step d) are then segregated, and are in general rejected. This can be done either manually or automatically by means of a robot.

In order to allow these semiconductor wafers to be segregated more easily, the z coordinate of the position of each mechanical defect is marked on the ingot section, preferably in an additional step e) between steps d) and f), for example by milling, grinding or drilling a depression. In the case of cylindrical ingot sections which are intended to be cut into semiconductor wafers at right angles to their outer surface, the marking is applied to the outer surface at the position $z_p$ determined in step d). Finally, in step h), all of those semiconductor wafers which have a marking on their circumference are segregated. This can be done, for example, manually on the basis of visual identification of the marking. Depending on how precisely the marking that has been applied to the outer surfaces matches the position $z_p$ of the mechanical defects, and depending on the thickness of the cut semiconductor wafers and the precision of the cutting process in step f), all that is necessary is to segregate those wafers which have the marking, or else the respectively adjacent wafers.

As an alternative to the application of the marking, those semiconductor wafers (and their numbers) which have at least one mechanical defect can be determined in step e) from the positions $z_p$ of the mechanical defects, and from the position of the cuts made in step f). These semiconductor wafers can finally be segregated manually or automatically by means of a robot, in step h). If the automization level of semiconductor wafer manufacture is sufficiently high, the material tracking system, for example, can determine the relevant wafer numbers. The material tracking system may, for example, use the position of the reference plane, which matches the first complete semiconductor wafer, and the sum of the pitch of the cuts (corresponding to the sum of the thickness of the cut semiconductor wafers and the loss of material caused in the cutting process) to determine the numbers of the semiconductor wafers affected. In this alternative as well, it may be necessary to segregate adjacent semiconductor wafers in order to be certain that all of the semiconductor wafers which have mechanical defects have been removed.

In order to avoid having to segregate an unnecessarily large number of semiconductor wafers, those semiconductor wafers which have at least one mechanical defect on the basis of the marking or calculated wafer number, as well as a defined number of adjacent semiconductor wafers, can be examined individually, in an additional step g) according to the prior art, for mechanical defects. This can be done, for example, by means of scanning ultrasound microscopy, infrared transmission measurement or X-ray absorption measurement. By way of example, the marked or calculated semiconductor wafers and their respectively closest neighbors are examined. Finally, the only semiconductor wafers which are segregated in step h) are those in which mechanical defects have actually been found in step g). All of the other semiconductor wafers which have been individually examined in step g) are fed back to the cassette or the magazine, and are processed further. This makes it possible on the one hand to avoid the time-consuming and costly examination of each individual semiconductor wafer, and on the other hand the unnecessary segregation of defect-free semiconductor wafers.

In order to effectively prevent the delivery of semiconductor wafers with cavities or other mechanical defects when the defect rates are low, a 100% inspection of all of the semiconductor wafers is in principle required when examination is carried out exclusively on the semiconductor wafers. The combination of the examination according to the invention of the ingot section in which the positions of the mechanical defects have been determined in advance with an examination of individual semiconductor wafers in which only a small number of wafers around the previously determined position are subsequently measured, makes it possible to ensure that all of the delivered semiconductor wafers are free of faults, with minimal measurement effort, and to maximize the semiconductor wafer yield. Subsequent measurement of individual semiconductor wafers in step g) is necessary only when a mechanical defect has been found in step d). The measurement effort for individual semiconductor wafers falls in a corresponding manner when the fault rate on the ingot sections falls.

Which of the described methods is preferred for segregation depends on the frequency of the mechanical defects, on the costs for production, examination and segregation of the semiconductor wafers, and on the costs of automation and material tracking.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method for the production of a multiplicity of semiconductor wafers, comprising
    a) producing a semiconductor ingot;
    b) cutting of the semiconductor ingot into ingot sections having at least one planar surface and a thickness, measured at right angles to the planar surface, of 1 cm to 100 cm:
    d) determining the position of mechanical defects in each ingot section, comprising scanning the planar surface of the ingot section by at least one ultrasound transducer which is coupled via a liquid coupling medium to the planar surface of the ingot section and, at each measurement point (x,y) produces at least one ultrasound pulse which is directed at the planar surface of the ingot section, and recording the ultrasound-pulse echo originating from the ingot section as a function of time, such that an echo from the planar surface, an echo from a surface, opposite the planar surface of the ingot section and further echoes are detected when mechanical defects are present, and determining the positions ($x_p$, $y_p$, $z_p$) of mechanical defects, in the ingot section from the further echoes, or by illuminating the ingot section from one end with infrared light, measuring the intensity of infrared light at an opposite end of the ingot section, and determining the positions ($x_p$, $y_p$, $z_p$) of mechanical defects, with the position of each mechanical defect being defined uniquely by coordinates $x_p$, $y_p$ on a plane parallel to the cuts to be made in step f), as well as by a coordinate $z_p$ at right angles to this plane;
    f) cutting the ingot sections into a multiplicity of semiconductor wafers with a thickness of 0.2 to 2 mm; and
    h) segregating those semiconductor wafers which contain the positions at which mechanical defects have been found.

2. The method of claim 1, wherein the thickness measured at right angles to the planar surface is 1 cm to 50 cm.

3. The method of claim 1, wherein the position ($z_p$) of a mechanical defect is determined in the z direction relative to a reference plane at right angles to the outer surface of the ingot section, the reference plane being independent of a wedge angle of the ingot section, and with the position of the reference plane being defined by the maximum distance ($z_{max}$) between the planar surface and a scanning plane, which is likewise at right angles to the outer surface and on which the at least one ultrasound head is located.

4. The method of claim 1, wherein the ingot sections produced in step b) are essentially in the form of a straight circular cylinder, and wherein, after step b), the outer surface of the ingot sections is ground in an additional step c).

5. The method of claim 1, wherein the position of mechanical defects in each ingot section is determined by illuminating one end of the ingot section with infrared radiation, and measuring the intensity of the transmitted infrared radiation on the other end of the ingot section.

6. The method of claim 1, wherein the z coordinate of the position of each mechanical defect on the ingot section is marked in an additional step e) between steps d) and f), and those semiconductor wafers which bear the marking after step f) are segregated in step h).

7. The method of claim 1, wherein, after step d), those semiconductor wafers which have at least one mechanical defect are determined in an additional step e) from the z coordinates of the positions of the mechanical defects and from the position of the cuts made in step f), and wherein these semiconductor wafers are segregated in step h).

8. The method of claim 1, wherein, after step d), those semiconductor wafers which have at least one mechanical defect are determined in an additional step e) from the z coordinates of the positions of the mechanical defects and from the position of the cuts made in step f), wherein these semiconductor wafers as well as a defined number of adjacent wafers are examined individually for mechanical defects in an additional step g), and wherein, in step h), all of those semiconductor wafers in which mechanical defects have been found in step g) are segregated.

9. The method of claim 1, wherein the ultrasound pulse is only partially focused or unfocused.

10. The method of claim 1, wherein the semiconductor material is a single-crystal semiconductor material.

11. The method of claim 10, wherein the semiconductor ingot which is composed of single-crystal semiconductor material is produced in step a) by Czochralski crucible pulling.

* * * * *